United States Patent
Huang et al.

(10) Patent No.: US 11,857,547 B2
(45) Date of Patent: *Jan. 2, 2024

(54) COMPOSITIONS AND METHODS FOR OPIOID ANTAGONIST DELIVERY

(71) Applicant: Purdue Pharma L.P., Stamford, CT (US)

(72) Inventors: Haiyong Hugh Huang, Princeton Junction, NJ (US); Manjunath S. Shet, White Plains, NY (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/195,142

(22) Filed: May 9, 2023

(65) Prior Publication Data
US 2023/0270741 A1    Aug. 31, 2023

Related U.S. Application Data

(63) Continuation of application No. 16/674,755, filed on Nov. 5, 2019.

(60) Provisional application No. 62/820,582, filed on Mar. 19, 2019, provisional application No. 62/756,322, filed on Nov. 6, 2018.

(51) Int. Cl.
| | |
|---|---|
| *A61K 31/395* | (2006.01) |
| *A61K 31/485* | (2006.01) |
| *A61K 47/02* | (2006.01) |
| *A61K 9/00* | (2006.01) |

(52) U.S. Cl.
CPC .......... *A61K 31/485* (2013.01); *A61K 9/0019* (2013.01); *A61K 47/02* (2013.01)

(58) Field of Classification Search
CPC .................................................. A61K 31/395
See application file for complete search history.

(56) References Cited

U.S. PATENT DOCUMENTS

| | | |
|---|---|---|
| 2004/0180916 A1 | 9/2004 | Levine |
| 2010/0041689 A1 | 2/2010 | Johnson et al. |
| 2010/0305500 A1 | 12/2010 | Lambert et al. |
| 2016/0310488 A1 | 10/2016 | Morillo et al. |
| 2017/0172522 A1 | 6/2017 | Insler et al. |
| 2020/0138805 A1* | 5/2020 | Huang ............... A61K 47/22 |

FOREIGN PATENT DOCUMENTS

| | | | |
|---|---|---|---|
| CN | 103655464 A | | 3/2014 |
| CN | 103705448 A | | 4/2014 |
| CN | 104922061 A | * | 9/2015 |
| CN | 104922061 A | | 9/2015 |
| WO | 2018093666 A1 | | 5/2018 |
| WO | 2017183559 A1 | | 2/2019 |

OTHER PUBLICATIONS

Prescribing Information: Revex (nalmefene hydrochloride injection) Jan. 2008.
International Search Report and Written Opinion for PCT/US2019/059852 dated Jan. 27, 2020, 18 pages.
Extended European Search Report for 19882381.7 dated Jul. 8, 2022, 7 pages.
Ushida, et al., "Intradermal administration of magnesium sulphate and magnesium chloride produces hypesthesia to mechanical but hyperalgesia to heat stimuli in humans", Journal of Neuroinflammation, 2009, 6 pgs. vol. 6, No. 25.
Durlach, et al., "Magnesium chloride or magnesium sulfate: a genuine question", Magnesium Research, 2005, pp. 187-192, vol. 18, No. 3.
Office Action for Japanese Patent Application No. 20221-521485 with English Translation, dated Oct. 20, 2023, 11 pages.

* cited by examiner

*Primary Examiner* — John S Kenyon
(74) *Attorney, Agent, or Firm* — Lowenstein Sandler LLP

(57) ABSTRACT

Disclosed in certain embodiments is a pharmaceutical formulation (e.g., parenteral formulation) comprising a therapeutically effective amount of nalmefene or a pharmaceutically acceptable salt thereof and a pharmaceutically acceptable adjuvant (e.g., parenterally acceptable adjuvant) that promotes the rate at which the nalmefene or salt thereof is more rapidly absorbed into the systemic circulation of a subject identified as in need thereof.

7 Claims, 5 Drawing Sheets

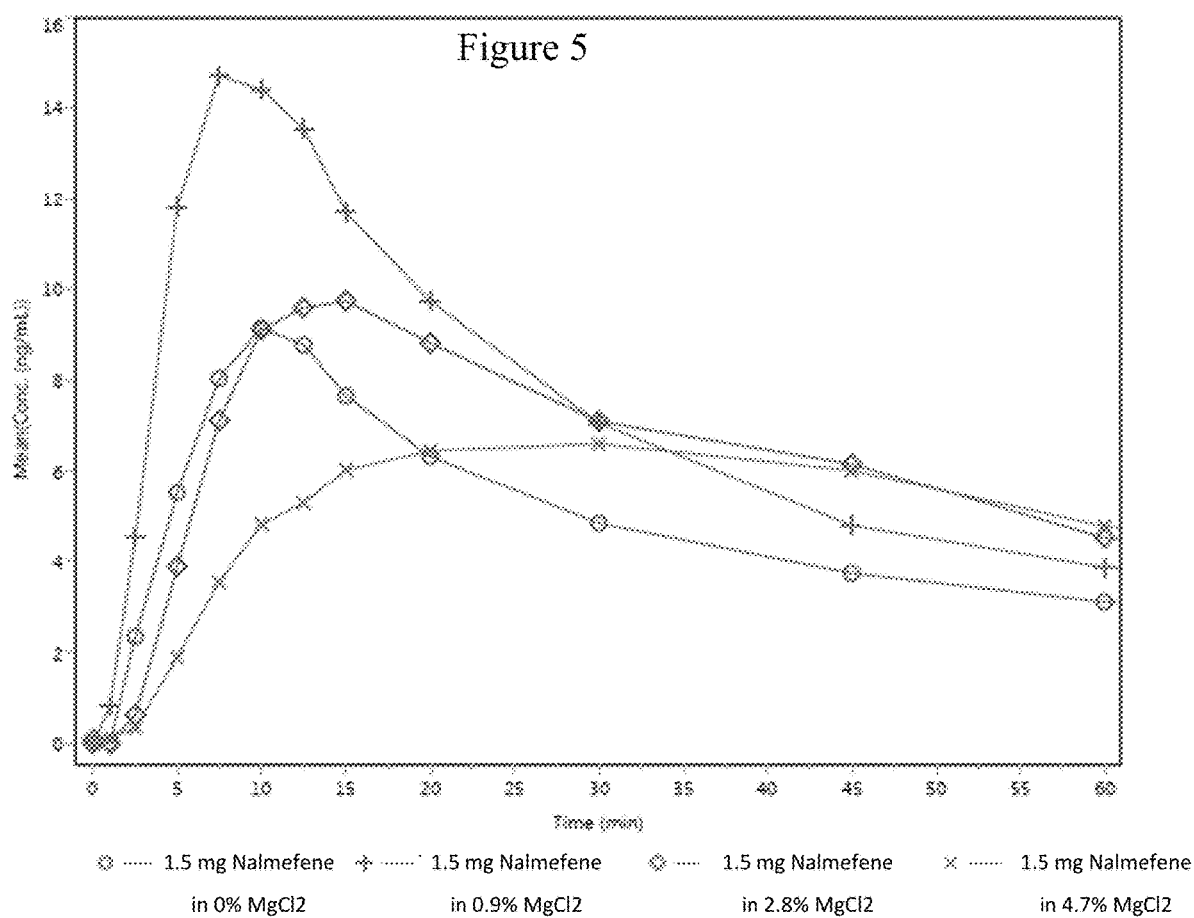

COMPOSITIONS AND METHODS FOR OPIOID ANTAGONIST DELIVERY

FIELD OF THE INVENTION

In certain embodiments, the present invention relates to the field of pharmaceutical compositions for rescuing a subject from an opioid overdose, methods of providing overdose rescue, pre-dosing a subject as protection against opioid overdose prior to entering an environment where opioid exposure may occur, methods for treating alcohol dependence, methods for treating constipation, and drug delivery systems thereof.

BACKGROUND OF THE INVENTION

Pharmaceutical products are sometimes subject to abuse. For example, a particular dose of opioid analgesic may be more potent when administered parenterally as compared to the same dose administered orally. Abusing a pharmaceutical product may result in an overdose that could be fatal. Also, potent opioids can be used as toxic chemical agents intentionally or unintentionally to cause death in humans through exposing humans to lethal doses through aerosolizing or other means of dispersal.

Symptoms of opioid overdose include, but not limited to, loss of consciousness, unresponsiveness to outside stimulus, being awake but unable to talk, respiratory depression or respiratory cessation, vomiting, limp body, pale or clammy skin, bluish fingernails and lips, slow heartbeat, erratic heartbeat, no heartbeat and eventual death.

To counteract opioid overdose effects, emergency personnel or others may administer an antidote such as an intramuscular injection of an opioid antagonist. Given that the administered antidote needs to be absorbed into the bloodstream, there inevitably will be a lag from the time of antidote administration to the time that the antidote reaches therapeutic levels sufficient to effectively counteract the effects of the opioid. Unfortunately, this lag time can result in the antidote treatment not being effective enough in sufficient time to prevent morbidity and mortality due to the overdose.

There exists a need in the art for a pharmaceutical composition for rescuing a subject from opioid overdose, and a method of rescuing a subject from an opioid overdose which method provides a rapid onset of action.

OBJECTS AND SUMMARY OF THE INVENTION

It is an object of certain embodiments of the present invention to provide a pharmaceutical composition (e.g., a parenteral formulation) for rescuing a subject from an opioid overdose, or for preventing (or reducing the risk in) a subject from experiencing an opioid overdose.

It is an object of certain embodiments of the present invention to provide a parenteral formulation for rescuing a subject from an opioid overdose, or for preventing (or reducing the risk in) a subject from experiencing an opioid overdose.

It is an object of certain embodiments of the present invention to provide a method for rescuing a subject from an opioid overdose, or for preventing (or reducing the risk in) a subject from experiencing an opioid overdose.

It is an object of certain embodiments of the present invention to provide a method of prophylactically administering a pharmaceutical composition as disclosed herein to a subject (e.g., a first responder or a member of law enforcement) who is at risk of being exposed to a toxic amount of an opioid agonist (e.g., fentanyl, sufentanyl, carfentanyl, or a salt or derivative thereof).

It is an object of certain embodiments of the present invention to provide a drug delivery system for rescuing a subject from an opioid overdose, or from preventing (or reducing the risk in) a subject (e.g., a first responder or a member of law enforcement) from experiencing an opioid overdose.

It is also an object of certain embodiments of the present invention to provide pharmaceutical compositions, drug delivery devices and methods for the treatment of alcohol dependence, constipation and other conditions that may be treated with opioid antagonists.

The above objects and others may be achieved by the present invention which in certain embodiments is directed to a pharmaceutical composition for providing opioid overdose rescue to a subject, or for preventing an opioid overdose in a subject. In certain embodiments, the pharmaceutical composition comprises a therapeutically effective amount of an opioid antagonist, and a parenterally acceptable absorption enhancing amount of an adjuvant that promotes, enhances, or quickens the systemic absorption rate of the opioid antagonist post intramuscular or subcutaneous injection. The adjuvant may be selected from appropriate absorption-enhancing agents currently known or those that would be readily appreciated by an ordinary skilled artisan (in formulation and medical fields) for such use. In certain non-limiting embodiments, the adjuvant comprises nitric oxide inducers, niacin, niacin derivatives, niacin metabolites phosphodiesterase inhibitors, angiotensin converting enzyme (ACE) inhibitors, angiotensin receptor blockers, calcium-channel blockers, nitrates or combinations thereof.

In certain embodiments, the opioid antagonist comprises naloxone, naltrexone, nalmefene, pharmaceutically acceptable salts thereof, or combinations thereof.

In certain embodiments, the pharmaceutical composition of the present invention comprises a therapeutically effective amount of nalmefene or a pharmaceutically acceptable salt thereof and an absorption-enhancing effective amount of a pharmaceutically acceptable adjuvant (e.g., parenterally acceptable adjuvant), wherein the composition provides a time to onset of action of the nalmefene of 5 minutes or less post intramuscular or subcutaneous injection to a subject experiencing, or at risk of experiencing an opioid agonist overdose.

In certain embodiments, the composition provides a mean time to maximum plasma concentration of nalmefene of about 2.0 hours or less post intramuscular injection to a population of healthy subjects or about 1.0 hour or less post subcutaneous injection to a population of healthy subjects.

In certain embodiments, the present invention is directed to an opioid overdose rescue method or an opioid overdose prevention method to a subject experiencing or at risk of experiencing an opioid (e.g., an opioid agonist) overdose, comprising intramuscularly, or subcutaneously administering to the subject a pharmaceutical composition as disclosed herein.

In certain embodiments, the present invention is directed to a drug delivery system comprising a device containing a pharmaceutical composition as disclosed herein. In one embodiment, such a device is suitable for delivering the pharmaceutical composition through injection. In certain embodiments, the composition is contained within a prefilled syringe, a vial, an injection pen, or an auto-injector.

BRIEF DESCRIPTION OF THE DRAWINGS

The above and other features of the present invention, their nature, and various advantages will become more apparent post consideration of the following detailed description, taken in conjunction with the accompanying drawings, in which:

FIG. 5 depicts the mean concentration as a function of time in human subjects treated intramuscularly with parenteral nalmefene formulations with various concentrations of $MgCl_2$, respectively.

DEFINITIONS

Figure 1:
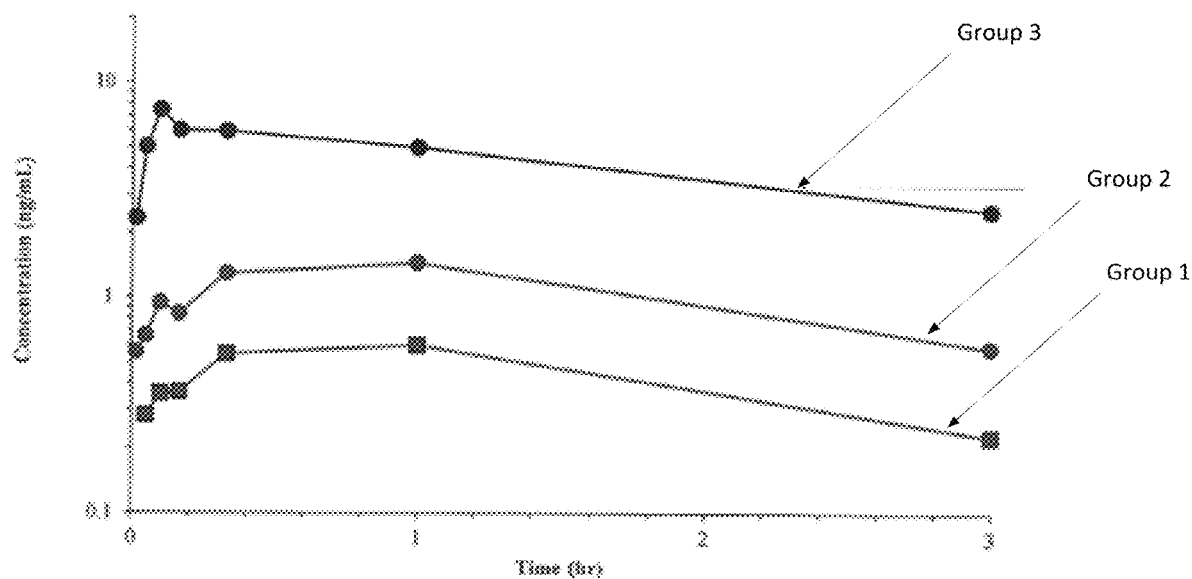
FIG. 1 depicts the comparative mean plasma concentration profiles of nalmefene alone at different doses (0.1 mg, 0.25 mg, and 1 mg) after intramuscular administration in three canine subjects.

As used herein, the singular forms "a," "an," and "the" include plural references unless the context clearly indicates otherwise. Thus, for example, reference to "an opioid antagonist" includes a single opioid antagonist as well as a mixture of two or more different opioid antagonists; and reference to an "excipient" includes a single excipient as well as a mixture of two or more different excipients, and the like.

As used herein, the term "about" in connection with a measured quantity or time, refers to the normal variations in that measured quantity or time, as expected by one of ordinary skill in the art in making the measurement and exercising a level of care commensurate with the objective of measurement. In certain embodiments, the term "about" includes the recited number±10%, such that "about 10" would include from 9 to 11, or "about 1 hour" would include from 54 minutes to 66 minutes.

As used herein, the term "active agent" refers to any material that is intended to produce a therapeutic, prophylactic, or other intended effect, whether or not approved by a government agency for that purpose. This term with respect to a specific agent includes the pharmaceutically active agent, and all pharmaceutically acceptable salts, solvates and crystalline forms thereof, where the salts, solvates and crystalline forms are pharmaceutically active.

As used herein, the terms "therapeutically effective" and an "effective amount" refer to that amount of an active agent or the rate at which it is administered needed to produce a desired therapeutic result.

The term "subject" refers to a human or animal, who has demonstrated a clinical manifestation of an opioid overdose suggesting the need for a rescue treatment, or who is at risk of being exposed to a toxic amount of an opioid. For example, in a first medical responder or law enforcement context, the subject is treated prophylactically with an opioid antagonist. The term "subject" may include a person or animal (e.g., a canine) who is a patient being appropriately treated by a medical caregiver with an opioid to treat or prevent pain. The term "subject" may also include a person or animal who is inappropriately using an opioid through misuse, abuse, or through inadvertent exposure. The term "subject" may also include a first responder (such as, an EMT responding to a case of opioid overdose), or a member of law enforcement, or a drug detecting canine, who are preparing to enter a locale where toxic amount of an opioid or opioids may be found. The term "subject" may also include any person who appears to a non-clinically trained bystander to be experiencing one or more behaviors (such as, unconsciousness, unresponsiveness, slowed breathing, or other behaviors suggestive of opioid-induced stupor or central nervous system depression) associated with excessive opioid exposure.

The terms "treatment of" and "treating" include the administration of an active agent(s) with the intent to lessen the severity of a condition.

The terms "prevention of" and "preventing" include the avoidance of the onset of a condition by a prophylactic administration of the active agent.

The term "condition" or "conditions" may refer to those medical conditions commonly recognized as the result of an opioid overdose, such as unresponsiveness, respiratory depression, vomiting, limp body, pale or clammy skin, bluish fingernails or lips, slow, erratic or no heartbeat, or a combination thereof, which can be treated, mitigated or prevented by a timely administration to a subject of an effective amount of an opioid antagonist. In certain embodiments, the term "condition" or "conditions" may refer to alcohol dependence or constipation.

The term "manic behavior" refers to a medical condition that may be characterized through physical and mental manifestations that may be expressed by one or more of the following symptoms: irritability, anxiety, aggressiveness, violence to self or others, hypersensitivity, hypervigilance, impulsivity, a compulsion to over-explain, sudden increase in energy levels, decreased need for sleep, hyperactivity, disorientation, incoherence, increase in risky behavior, inattentiveness, delusions, inflated self-esteem, grandiosity, distractibility, etc.

The term "combative behavior" refers to a subject's manifestation of violent, irritable, and/or aggressive symptoms that could result in physical or mental harm to the subject and/or to his surroundings and/or to a person administering a medical treatment, such as administration of an opioid antagonist.

The term "adjuvant" refers to an agent that is incorporated into a pharmaceutical composition to enhance the absorption of an active agent, e.g., by increasing $C_{max}$, shortening $T_{max}$, or increasing bioavailability, or a combination thereof. An adjuvant may be inactive in all other respects or may provide an intended or unintended pharmacological effect in addition to enhancing the absorption of an active agent.

A "toxic amount of an opioid agonist" may be understood by one skilled in the art (e.g., a clinician, a first responder, and the like) as the amount of opioid agonist which would most likely cause a serious adverse event (such as, respiratory failure, unresponsiveness, and slow breathing etc.). Such toxic amount may vary from one opioid agonist to another and from one individual subject to another.

The term "$T_{1/2}$" refers to the time for the plasma concentration of an active agent to decrease by half.

Recitation of ranges of values herein is merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to illuminate certain materials and methods and does not pose a limitation on scope. No language in the specification should be construed as indicating any non-claimed element as essential to the practice of the disclosed materials and methods.

DETAILED DESCRIPTION

Dosage Forms and Pharmaceutical Compositions

According to various embodiments, the present invention is related to a pharmaceutical composition for opioid overdose rescue or prevention. In certain embodiments, the invention is directed to a pharmaceutical composition comprising a therapeutically effective amount of an opioid antagonist and a pharmaceutically acceptable adjuvant (e.g., a parenterally acceptable adjuvant) that promotes the absorption rate of the opioid antagonist post intramuscular or subcutaneous injection. The adjuvant may comprise nitric oxide inducers, niacin, niacin derivatives, niacin metabolites, phosphodiesterase inhibitors, angiotensin converting enzyme (ACE) inhibitors, angiotensin receptor blockers, calcium channel blockers, nitrates or combinations thereof. Such a pharmaceutical composition can provide for a quicker onset of action of the opioid antagonist as compared to the same pharmaceutical composition without the adjuvant.

The opioid antagonist can be any opioid antagonist currently known or those that would be readily appreciated by an ordinary skilled artisan (in formulation and medical fields) for such use that effectively counteracts or prevents an opioid overdose. In certain embodiments, the opioid antagonist comprises naloxone, naltrexone, nalmefene, pharmaceutically acceptable salts thereof, or combinations thereof. In certain embodiments, the opioid antagonist is nalmefene.

In certain embodiments, the invention is directed to a pharmaceutical composition comprising a therapeutically effective amount of nalmefene or a pharmaceutically acceptable salt thereof and a parenterally acceptable adjuvant, wherein the formulation provides a time to onset of action (i.e., the first detectable therapeutic effect associated with administration of an opioid antagonist, e.g., detectable lessening or reduction of any of the symptoms associated with opioid overdose) of less than 5 minutes post intramuscular or subcutaneous injection to a subject experiencing an opioid agonist overdose, or pretreating against potential opioid agonist exposure.

In certain embodiments, the pharmaceutical composition provides a time to onset of action (i.e., counteracting at least one symptom of an opioid overdose) of about 4 minutes or less, about 3 minutes or less, about 2 minutes or less or about 1 minute or less post intramuscular or subcutaneous injection to a subject experiencing an opioid agonist overdose or needing pretreatment against potential opioid agonist exposure (i.e., prophylactic treatment). In certain embodiments, the pharmaceutical composition provides a time to onset of action (i.e., counteracting, e.g., with clinical manifestation, at least one symptom of an opioid overdose) from greater than about 5 seconds, greater than about 10 seconds, greater than about 15 seconds, greater than about 30 seconds, greater than about 45 seconds, or greater than about 1 minute to less than about 5 minutes, about 4 minutes or less, about 3 minutes or less, or about 2 minutes or less post intramuscular or subcutaneous injection to a subject experiencing an opioid agonist overdose or needing pretreatment against potential opioid agonist exposure (i.e., prophylactic treatment).

In other embodiments, the invention is directed to a pharmaceutical composition comprising a therapeutically effective amount of nalmefene or a pharmaceutically acceptable salt thereof and a parenterally acceptable adjuvant, wherein the formulation provides a mean time to maximum plasma concentration of nalmefene of about 2.0 hours or less post intramuscular injection to a population of subjects (e.g., otherwise healthy subjects) or about 1 hour or less post subcutaneous injection to a population of subjects (e.g., otherwise healthy subjects).

In other embodiments, the invention is directed to a pharmaceutical composition comprising a therapeutically effective amount of nalmefene or a pharmaceutically acceptable salt thereof and a parenterally acceptable adjuvant, wherein the formulation provides a mean time to maximum plasma concentration of nalmefene of about 2 hours or less, about 1.5 hours or less, about 1 hour or less, about 0.5 hour or less, about 20 minutes or less, about 15 minutes or less, or about 10 minutes or less, post intramuscular injection to a population of subjects (e.g., otherwise healthy subjects). In other embodiments, the formulation provides a mean time to maximum plasma concentration of nalmefene from about 0.1 hour or more, about 0.2 hour or more, about 0.3 hour or more, or about 0.4 hour or more to any of about 2.0 hours or less, about 1.5 hours or less, about 1 hour or less, or about 0.5 hour or less post intramuscular injection to a population of subjects (e.g., otherwise healthy subjects).

In other embodiments, the invention is directed to a pharmaceutical composition comprising a therapeutically effective amount of nalmefene or a pharmaceutically acceptable salt thereof and a parenterally acceptable adjuvant, wherein the formulation provides an individual time to maximum plasma concentration of nalmefene of about 2 hours or less, about 1.5 hours or less, about 1 hour or less, about 0.5 hour or less, about 20 minutes or less, about 15 minutes or less, or about 10 minutes or less, post intramuscular injection or post subcutaneous injection to a subject (e.g., otherwise healthy subject). In other embodiments, the formulation provides an individual time to maximum plasma concentration of nalmefene from about 0.1 hour or more, about 0.2 hour or more, about 0.3 hour or more, or about 0.4 hour or more to any of about 2.0 hours or less, about 1.5 hours or less, about 1 hour or less, or about 0.5 hour or less post intramuscular injection or post subcutaneous injection to a subject (e.g., otherwise healthy subject).

In certain embodiments, the invention is directed to a pharmaceutical composition comprising a therapeutically effective amount of nalmefene or a pharmaceutically acceptable salt thereof and a parenterally acceptable adjuvant, wherein the formulation provides a mean $T_{1/2}$ of about 5 hours to about 20 hours, of about 7 hours to about 15 hours, of about 8 hours to about 12 hours or of about 9 hours to about 10 hours post intramuscular injection or post subcutaneous injection to a population of subjects (e.g., otherwise healthy subjects).

In other embodiments, the invention is directed to a pharmaceutical composition comprising a therapeutically effective amount of nalmefene or a pharmaceutically acceptable salt thereof and a parenterally acceptable adjuvant, wherein the formulation provides a mean time to maximum plasma concentration of nalmefene of about 1 hour or less, about 0.5 hour or less, about 20 minutes or less, about 15 minutes or less, or about 10 minutes or less, post subcutaneous injection to a population of subjects (e.g., otherwise healthy subjects). In other embodiments, the formulation provides a mean time to maximum plasma concentration of nalmefene from about 0.1 hour or more, about 0.2 hour or more, about 0.3 hour or more, or about 0.4 hour or more to about 1.0 hour or about 0.5 hours or less post subcutaneous injection to a population of subjects (e.g., otherwise healthy subjects).

In certain embodiments, the composition provides a mean time to maximum plasma concentration of nalmefene of about 3.0 hours or less, about 2.5 hours or less, about 2.0 hours or less, about 1 hour or less, about 0.5 hours or less, about 15 minutes or less, about 12 minutes or less, about 10 minutes or less, or about 8 minutes or less post intramuscular or subcutaneous injection to a population of subjects (e.g., otherwise healthy subjects) and also provides an onset of therapeutic action of less than 5 minutes, about 4 minutes or less, about 3 minutes or less, about 2 minutes or less or about 1 minute or less post intramuscular or subcutaneous injection to a subject experiencing an opioid agonist overdose or needing pretreatment due to potential opioid agonist exposure.

In other embodiments, the composition provides a mean time to maximum plasma concentration of nalmefene of about 2.0 hours or less post intramuscular injection to a population of subjects (e.g., healthy subjects, or otherwise healthy subjects) or about 1.0 hour or less post subcutaneous injection to a population of subjects (e.g., healthy subjects, or otherwise healthy subjects) and also provides an onset of therapeutic action of about 15 minutes or less, about 12 minutes or less, about 10 minutes or less, about 8 minutes or less, about 5 minutes or less, 4 minutes or less, about 3 minutes or less, about 2 minutes or less or about 1 minute or less post intramuscular or subcutaneous injection to a subject experiencing an opioid agonist overdose or needing pretreatment due to a potential opioid agonist exposure.

In certain embodiments, the invention is directed to a pharmaceutical composition comprising a therapeutically effective amount of nalmefene or a pharmaceutically acceptable salt thereof and a parenterally acceptable adjuvant, wherein the formulation provides a mean time to maximum plasma concentration of nalmefene ($T_{max}$) that is shorter than the mean time to maximum plasma concentration of nalmefene of a comparative formulation without the adjuvant, post intramuscular or subcutaneous injection to a population of subjects (e.g., healthy subjects, or otherwise healthy subjects). For instance, the mean $T_{max}$ of the present invention may be about 1.1 times shorter, about 1.2 times shorter, about 1.3 times shorter, about 1.4 times shorter, about 1.5 times shorter, about 1.6 times shorter, about 1.7 times shorter, about 1.8 times shorter, about 1.9 times shorter, or about 2 times shorter than that of a comparative formulation without the adjuvant.

In certain embodiments, the invention is directed to a pharmaceutical composition comprising a therapeutically effective amount of nalmefene or a pharmaceutically acceptable salt thereof and a parenterally acceptable adjuvant, wherein the formulation provides a mean $T_{1/2}$ that is longer than the mean time for the plasma concentration of nalmefene of a comparative formulation without the adjuvant to decrease by half, post intramuscular or subcutaneous injection to a population of subjects (e.g., healthy subjects, or otherwise healthy subjects). For instance, the $T_{1/2}$ of the present invention may be about 1.1 times longer, about 1.2 times longer, about 1.3 times longer, about 1.4 times longer, about 1.5 times longer, about 1.6 times longer, about 1.7 times longer, about 1.8 times longer, about 1.9 times longer, or about 2 times longer than that of a comparative formulation without the adjuvant.

In certain embodiments, the invention is directed to a pharmaceutical composition comprising a therapeutically effective amount of nalmefene or a pharmaceutically acceptable salt thereof and a parenterally acceptable adjuvant, wherein the formulation provides a mean maximum plasma concentration of nalmefene ($C_{max}$) of 1 ng/mL to about 50 ng/mL, about 5 ng/mL to about 20 ng/mL, about 7 ng/mL to about 18 ng/mL, about 9 ng/mL to about 16 ng/mL, about 2 ng/mL to about 25 ng/mL, about 4 ng/mL to about 21 ng/mL, about 10 ng/mL to about 21 ng/mL, about 5 to about 18 ng/mL, about 4 ng/mL to about 10 ng/mL, or about 12.5 ng/mL to about 21 ng/mL, post intramuscular or subcutaneous injection to a population of subjects (e.g., healthy subjects, or otherwise healthy subjects).

In certain embodiments, the invention is directed to a pharmaceutical composition comprising a therapeutically effective amount of nalmefene or a pharmaceutically acceptable salt thereof and a parenterally acceptable adjuvant, wherein the formulation provides a mean maximum plasma concentration of nalmefene ($C_{max}$) that is greater than the mean maximum plasma concentration of nalmefene of a comparative formulation without the adjuvant, post intramuscular or subcutaneous injection to a population of subjects (e.g., healthy subjects, or otherwise healthy subjects). For instance, $C_{max}$ may be about 1.1 times greater, about 1.2 times greater, about 1.3 times greater, about 1.4 times greater, about 1.5 times greater, about 1.6 times greater, about 1.7 times greater, about 1.8 times greater, about 1.9 times greater, or about 2 times greater than that of a comparative formulation without the adjuvant.

In certain embodiments, the invention is directed to a pharmaceutical composition comprising a therapeutically effective amount of nalmefene or a pharmaceutically acceptable salt thereof and a parenterally acceptable adjuvant, wherein the formulation provides an individual maximum plasma concentration of nalmefene ($C_{max}$) of about 1 ng/mL to about 50 ng/mL, about 2 ng/mL to about 25 ng/mL, about 4 ng/mL to about 21 ng/mL, about 10 ng/mL to about 21 ng/mL, about 5 to about 18 ng/mL, about 4 ng/mL to about 10 ng/mL, or about 12.5 ng/mL to about 21 ng/mL, post intramuscular or subcutaneous injection to a subject (e.g., a healthy subject, or an otherwise healthy subject).

In certain embodiments, the invention is directed to a pharmaceutical composition comprising a therapeutically effective amount of nalmefene or a pharmaceutically acceptable salt thereof and a parenterally acceptable adjuvant, wherein the formulation provides a mean plasma concentration of nalmefene five minutes (0.083 hours) after administration ($AUC_{0-5}$) of about 0.20 ng/mL·hr to about 0.50 ng/mL·hr, about 0.30 ng/mL·hr to about 0.40 ng/mL·hr, about 0.32 ng/mL·hr to about 0.35 ng/mL·hr, about 0.03 ng/mL·hr to about 1.2 ng/mL·hr, about 0.07 ng/mL·hr to about 1.1 ng/mL·hr, about 0.12 ng/mL·hr to about 1 ng/mL·hr, about 0.5 ng/mL·hr to about 1 ng/mL·hr, greater than about 0.03 ng/mL·hr, greater than about 0.07 ng/mL·hr, greater than about 0.12 ng/mL·hr, or greater than about 0.5 ng/mL·hr, post intramuscular injection or subcutaneous injection to a population of subjects (e.g., healthy subjects, or otherwise healthy subjects).

In certain embodiments, the invention is directed to a pharmaceutical composition comprising a therapeutically effective amount of nalmefene or a pharmaceutically acceptable salt thereof and a parenterally acceptable adjuvant, wherein the formulation provides a mean plasma concentration of nalmefene ten minutes (0.167 hours) after administration ($AUC_{0-10}$) in about 1.00 ng/mL·hr to about 2.00 ng/mL·hr, about 1.20 ng/mL·hr to about 1.80 ng/mL·hr, about 1.40 ng/mL·hr to about 1.60 ng/mL·hr, about 0.2 ng/mL·hr to about 3 ng/mL·hr, about 0.3 ng/mL·hr to about 2.8 ng/mL·hr, about 0.7 ng/mL·hr to about 2.5 ng/mL·hr, about 1.3 ng/mL·hr to about 2.5 ng/mL·hr, greater than about 0.2 ng/mL·hr, greater than about 0.3 ng/mL·hr, greater than about 0.7 ng/mL·hr, or greater than about 1.3 ng/mL·hr, post intramuscular injection or subcutaneous injection to a population of subjects (e.g., healthy subjects, or otherwise healthy subjects).

In certain embodiments, the invention is directed to a pharmaceutical composition comprising a therapeutically effective amount of nalmefene or a pharmaceutically acceptable salt thereof and a parenterally acceptable adjuvant, wherein the formulation provides a mean plasma concentration of nalmefene fifteen minutes (0.25 hours) after administration ($AUC_{0-15}$) of about 1.6 ng/mL·hr to about 3.5 ng/mL·hr, about 2.0 ng/mL·hr to about 3.0 ng/mL·hr, about 2.4 ng/mL·hr to about 2.8 ng/mL·hr, about 0.5 ng/mL·hr to about 4.2 ng/mL·hr, about 0.8 ng/mL·hr to about 4 ng/mL·hr, about 1.5 ng/mL·hr to about 3.8 ng/mL·hr, greater than about 0.5 ng/mL·hr, greater than about 0.8 ng/mL·hr, or greater than about 1.5 ng/mL·hr, post intramuscular injection or subcutaneous injection to a population of subjects (e.g., healthy subjects, or otherwise healthy subjects).

In certain embodiments, the invention is directed to a pharmaceutical composition comprising a therapeutically effective amount of nalmefene or a pharmaceutically acceptable salt thereof and a parenterally acceptable adjuvant, wherein the formulation provides a mean plasma concentration of nalmefene twenty minutes (0.333 hours) after administration ($AUC_{0-20}$) of about 2.1 ng/mL·hr to about 5.0 ng/mL·hr, about 2.8 ng/mL·hr to about 4.0 ng/mL·hr, or about 3.3 ng/mL·hr to about 3.7 ng/mL·hr, about 0.5 ng/mL·hr to about 5.8 ng/mL·hr, about 1.2 ng/mL·hr to about 5.3 ng/mL·hr, about 2 ng/mL·hr to about 5 ng/mL·hr, greater than about 0.5 ng/mL·hr, greater than about 1.2 ng/mL·hr, or greater than about 2 ng/mL·hr, post intramuscular injection or subcutaneous injection to a population of subjects (e.g., healthy subjects, or otherwise healthy subjects).

In certain embodiments, the invention is directed to a pharmaceutical composition comprising a therapeutically effective amount of nalmefene or a pharmaceutically acceptable salt thereof and a parenterally acceptable adjuvant, wherein the formulation provides an individual plasma concentration of nalmefene five minutes (0.083 hours) after administration of about 0.03 ng/mL·hr to about 1.2 ng/mL·hr, about 0.07 ng/mL·hr to about 1.1 ng/mL·hr, about 0.12 ng/mL·hr to about 1 ng/mL·hr, or about 0.5 ng/mL·hr to about 1 ng/mL·hr, post intramuscular injection or subcutaneous injection to a subject (e.g., a healthy subject, or an otherwise a healthy subject). In certain embodiments, the formulation provides an individual plasma concentration of nalmefene at greater than about 0.03 ng/mL·hr, greater than about 0.07 ng/mL·hr, greater than about 0.12 ng/mL·hr, or greater than about 0.5 ng/mL·hr, at about five minutes (0.083 hours) post administration via intramuscular injection or subcutaneous injection to a subject (e.g., a healthy subject, or an otherwise a healthy subject).

In certain embodiments, the invention is directed to a pharmaceutical composition comprising a therapeutically effective amount of nalmefene or a pharmaceutically acceptable salt thereof and a parenterally acceptable adjuvant, wherein the formulation provides an individual plasma concentration of nalmefene at about 0.2 ng/mL·hr to about 3 ng/mL·hr, about 0.3 ng/mL·hr to about 2.8 ng/mL·hr, about 0.7 ng/mL·hr to about 2.5 ng/mL·hr, or about 1.3 ng/mL·hr to about 2.5 ng/mL·hr, at about ten minutes (0.167 hours) after administration via an intramuscular injection or subcutaneous injection to a subject (e.g., a healthy subject, or an otherwise a healthy subject). In certain embodiments, the formulation provides an individual plasma concentration of nalmefene at greater than about 0.2 ng/mL·hr, greater than about 0.3 ng/mL·hr, greater than about 0.7 ng/mL·hr, or greater than about 1.3 ng/mL·hr, at about ten minutes (0.167 hours) after administration via an intramuscular injection or subcutaneous injection to a subject (e.g., a healthy subject, or an otherwise a healthy subject).

In certain embodiments, the invention is directed to a pharmaceutical composition comprising a therapeutically effective amount of nalmefene or a pharmaceutically acceptable salt thereof and a parenterally acceptable adjuvant, wherein the formulation provides an individual plasma concentration of nalmefene at about 0.5 ng/mL·hr to about 4.2 ng/mL·hr, about 0.8 ng/mL·hr to about 4 ng/mL·hr, or about 1.5 ng/mL·hr to about 3.8 ng/mL·hr, at fifteen minutes (0.25 hours) after administration via an intramuscular injection or subcutaneous injection to a subject (e.g., a healthy subject, or an otherwise healthy subject). In certain embodiments, the formulation provides an individual plasma concentration of nalmefene at greater than about 0.5 ng/mL·hr, greater than about 0.8 ng/mL·hr, or greater than about 1.5 ng/mL·hr, at fifteen minutes (0.25 hours) after administration via an intramuscular injection or subcutaneous injection to a subject (e.g., a healthy subject, or an otherwise a healthy subject).

In certain embodiments, the invention is directed to a pharmaceutical composition comprising a therapeutically effective amount of nalmefene or a pharmaceutically acceptable salt thereof and a parenterally acceptable adjuvant, wherein the formulation provides an individual plasma concentration of nalmefene at about 0.5 ng/mL·hr to about 5.8 ng/mL·hr, about 1.2 ng/mL·hr to about 5.3 ng/mL·hr, or about 2 ng/mL·hr to about 5 ng/mL·hr, at twenty minutes (0.333 hours) after administration via an intramuscular injection or subcutaneous injection to a subject (e.g., a healthy subject, or an otherwise a healthy subject). In certain embodiments, the formulation provides an individual plasma concentration of nalmefene at greater than about 0.5 ng/mL·hr, greater than about 1.2 ng/mL·hr, or greater than about 2 ng/mL·hr, twenty minutes (0.333 hours) after administration via an intramuscular injection or subcutaneous injection to a subject (e.g., a healthy subject, or an otherwise a healthy subject).

In certain embodiments, pharmacokinetic values described herein are obtained from a subject or a population of subjects having any of the pharmaceutical compositions disclosed herein administered intramuscularly to their deltoid. In other embodiments, pharmacokinetic values described herein are obtained from a subject or a population of subjects having any of the pharmaceutical compositions disclosed herein administered intramuscularly to their thigh.

In certain embodiments, the pharmacokinetic values described herein may be obtained from an individual subject (healthy or in therapeutic need thereof) or from a plurality of subjects (healthy or in therapeutic need thereof) post a parenteral administration of any of the pharmaceutical compositions disclosed herein.

The role of the adjuvant is to promote or quicken the systemic absorption rate of the opioid antagonist (e.g., nalmefene or a pharmaceutically acceptable salt thereof) post intramuscular or subcutaneous injection. In certain embodiments, the adjuvant is a vasodilator. The vasodilator may be an angiotensin converting enzyme (ACE) inhibitor, an angiotensin receptor blocker, a calcium channel blocker, a nitrate or magnesium chloride.

In some embodiments, the adjuvant is magnesium chloride and is present in the pharmaceutical composition, e.g., at a concentration ranging from about 0.1% (w/v) to about 50% (w/v), from about 0.1% (w/v) to about 30% (w/v), from about 5% (w/v) to about 30% (w/v), from about 1% (w/v) to about 25% (w/v), from about 15% (w/v) to about 25% (w/v), from about 0.5% (w/v) to about 5% (w/v), from about 0.5% (w/v) to about 1% (w/v), from about 0.5% (w/v) to about 1.5% (w/v), from about 0.5% (w/v) to about 3.5% (w/v), from about 0.5% (w/v) to about 3.0% (w/v), from about 2.5% (w/v) to about 3% (w/v), from about 2.0% (w/v) to about 4% (w/v), from about 2.0% (w/v) to about 3.0% (w/v), from about 4.5% (w/v) to about 5% (w/v), about 0.9% (w/v), about 1% (w/v), about 2.8% (w/v), about 3% (w/v), about 4.7% (w/v), about 5% (w/v), about 10% (w/v), about 15% (w/v), or about 20% (w/v) of magnesium chloride in the pharmaceutical composition.

In certain embodiments, the adjuvant may comprise a vasodilator that is an ACE inhibitor, e.g., enalapril, captopril, lisinopril, benazepril, enalaprilat, espirapril, fosinopril, moexipril, quinapril, ramipril, perindopril, trandolapril, pharmaceutically acceptable salts thereof or combinations thereof. In certain embodiments, the adjuvant may comprise a vasodilator that is an angiotensin receptor blocker, e.g., valsartan, losartan, irbesartan, telmisartan, eprosartan, candesartan, olmesartan, saprisartan, tasosartan, elisartan, pharmaceutically acceptable salts thereof or combinations thereof. In certain embodiments, the adjuvant may comprise a vasodilator that is a calcium channel blocker, e.g., amlodipine, anipamil, barnidipine, benidipine, bepridil, darodipine, diltiazem, efonidipine, felodipine, isradipine, lacidipine, lercanidipine, lidoflazine, manidipine, mepirodipine, nicardipine, nifedipine, niludipine, nilvadipine, nimodipine, nisoldipine, nitrendipine, perhexiline, tiapamil, verapamil, pharmaceutically acceptable salts thereof or combinations thereof.

In certain embodiments, the adjuvant comprises a nitric oxide inducer. The nitric oxide inducer can be, e.g., an amino acid (e.g., arginine). The nitric oxide inducer can be, without limitation, L-arginine, L-homoarginine, N-hydroxy-L-arginine, nitrosated analogs thereof, nitrosylated analogs thereof, precursors thereof or combinations thereof. The nitrosated analogs may be, e.g., nitrosated L-arginine, nitrosated N-hydroxy-L-arginine, nitrosated L-homoarginine or combinations thereof. The nitrosylated analogs may be, e.g., nitrosylated L-arginine, nitrosylated N-hydroxy-L-arginine, nitrosylated L-homoarginine or combinations thereof. Also, the precursor may be, e.g., citrulline, ornithine, glutamine, lysine or combinations thereof. In one embodiment, the adjuvant is L-arginine and is present in the pharmaceutical composition, e.g., at a concentration ranging from about 0.1% to about 50%, from about 5% to about 30%, from about 15% to about 25%, or about 20% (w/v) of L-arginine per pharmaceutical composition.

In certain embodiments, the nitric oxide inducer comprises arginase inhibitors, substrates for nitric oxide synthase, nitroglycerin, amyl nitrate, or combinations thereof. In certain embodiments, the arginase inhibitor comprises, e.g., N-hydroxy-L-arginine, 2(S)-amino-6-boronohexanoic or combinations thereof. In other embodiments, the substrate for nitric oxide synthase comprises cytokines, adenosine, bradykinin, calreticulin, bisacodyl, phenolphthalein, or combinations thereof.

In other embodiments, the adjuvant comprises niacin, a niacin derivative, a niacin metabolite, or a combination thereof. The niacin derivative may be acifran, acipimox, niceritrol, isonicotinic acid, isonicotinohydrazide, pyridine carboxylic acid derivatives, 3-pyridine acetic acid, 5-methylnicotinic acid, pyridazine-4-carboxylic acid, pyrazine-2-carboxylic acid, or combinations thereof. In certain embodiments, the niacin derivative is an ester of nicotinic acid, e.g., an alkyl ester of nicotinic acid such as methyl nicotinate. In other embodiments, the niacin metabolite comprises nicotinuric acid, nicotinamide, 6-hydroxy nicotinamide, N-methylnicotinamide, nicotinamide-N-oxide, N-methyl-2-pyridone-5-carboxamide, N-methyl-4-pyridone-5-carboxamide, or combinations thereof. In certain embodiments, the adjuvant is niacin and is present in the pharmaceutical composition at a concentration ranging from about 0.1% to about 15%, from about 0.5% to about 5%, about 1%, about 2%, or about 3% (w/v) of niacin per pharmaceutical composition.

In certain embodiments, the adjuvant comprises a phosphodiesterase inhibitor. The phosphodiesterase inhibitor comprises phosphodiesterase 1 inhibitors, phosphodiesterase 2 inhibitors, phosphodiesterase 3 inhibitors, phosphodiesterase 4 inhibitors, phosphodiesterase 5 inhibitors, or combinations thereof. In other embodiments, the phosphodiesterase inhibitor comprises vinpocetine, EHNA (erythro-9-(2-hydroxy-3-nonyl)adenine), anagrelide, enoximine, cilomilast, etazolate, glaucine, ibudilast, mesembrine, rolipram, pentoxifylline, piclamilast, dipyridamole, acetildenafil, avanafil, sildenafil, tadalafil, udenafil, vardenafil, milrinone, amrinone or combinations thereof.

In certain embodiments, the pharmaceutical composition and dosage forms disclosed herein comprise from about 0.1%, about 0.2%, about 0.3%, about 0.4%, about 0.5%, about 0.6%, about 0.7%, about 0.8%, about 0.9%, or about 1% to about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 60%, about 70%, or about 80% (w/v) of an adjuvant per dosage form. In certain embodiments, the pharmaceutical composition and dosage forms disclosed herein comprises from about 0.1% to about 30%, from about 0.5% to about 25%, or from about 1% to about 20% (w/v) of an adjuvant per dosage form.

In certain embodiments, the pharmaceutical composition may further comprise a therapeutically effective amount of an antipsychotic agent to counteract manic behavior that may be triggered by the administration of the opioid antagonist and the sudden awakening of the subject from overdose to unfamiliar surroundings, possibly restrained in handcuffs or to a hospital bed, and possibly in the presence of rescue or law enforcement personnel (such as first responders including ambulance operators, nurses, doctors, police officers, firefighters, Good Samaritans, etc.). Post intramuscular or subcutaneous administration of the pharmaceutical composition, a therapeutically effective amount of the antipsychotic agent is preferably bioavailable post opioid rescue or within a short time (e.g., about 12 minutes or less, about 10 minutes or less, about 8 minutes or less, about 5 minutes or less, about 3 minutes or less, or about 1 minute or less) after opioid overdose rescue. In this manner, when a subject awakens, e.g., after being rescued, the antipsychotic agent may inhibit or reduce any combative behavior that the subject would otherwise manifest post awakening. In some embodiments, the manic behavior comprises a physically combative behavior by the subject.

Active Agents

The delivery systems and pharmaceutical compositions disclosed herein include various active agents or their pharmaceutically acceptable salts. Pharmaceutically acceptable salts include, but are not limited to, inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparginate, glutamate and the like, and metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like.

The delivery systems and pharmaceutical compositions disclosed herein include an opioid antagonist. The opioid antagonist may comprise naloxone, naltrexone, nalmefene, cyclazocine, levallorphan, samidorphan, methylsamidorphan, nalodeine, alvimopan, methylnaltrexone, naloxegol, naloxol, 6β-naltrexol, axelopran, bevenopran, naldemedine, cyprodime, naltrindole, norbinaltorphimine, pharmaceutically acceptable salts thereof, or combinations thereof.

In certain embodiments, the opioid antagonist comprises naloxone, naltrexone, nalmefene, pharmaceutically acceptable salts thereof and combinations thereof. In one embodiment, the opioid antagonist comprises naloxone or a pharmaceutically acceptable salt thereof. In another embodiment, the opioid antagonist comprises naltrexone or a pharmaceutically acceptable salt thereof. In a further embodiment, the opioid antagonist comprises nalmefene or a pharmaceutically acceptable salt thereof (e.g., nalmefene hydrochloride).

In certain embodiments, the opioid antagonist is nalmefene or a pharmaceutically acceptable salt thereof which is present in a pharmaceutical formulation at about 0.05 mg/ml to about 10 mg/ml, about 0.1 mg/ml to about 5 mg/ml, about 0.3 mg/ml to about 2.5 mg/ml, about 0.5 mg/ml to about 1.5 mg/ml, about 2 mg/ml to about 3 mg/ml, about 1.25 mg/ml, about 1 mg/ml, about 1.5 mg/ml, about 1.75 mg/ml, or about 2.0 mg/ml, or about 2.5 mg/ml, and is adapted for parenteral administration.

In certain embodiments, the pharmaceutical formulation (e.g., parenteral formulation) may provide an opioid antagonist (e.g., nalmefene or a pharmaceutically acceptable salt thereof) dose ranging from any of about 0.25 mg, about 0.5 mg, about 0.75 mg, about 1 mg, about 1.25 mg, about 1.5 mg, about 1.75 mg, about 2.0 mg, about 2.25 mg, or about 2.5 mg to any of about 2.75 mg, about 3.0 mg, about 3.25 mg, about 3.5 mg, about 3.75 mg, about 4.0 mg, about 4.25 mg, about 4.5 mg, about 4.75 mg, or about 5.0 mg.

According to certain embodiments, the delivery systems and pharmaceutical compositions disclosed herein further comprise an anti-psychotic agent. In some embodiments, the anti-psychotic agent comprises butyrophenones, diphenylbutylpiperidines, phenothiazines, thioxanthenes, benzamides, tricyclics, benzisoxazoles or benzisothiazoles, phenylpiperazines, quinolinones, blonanserin, pimavanserin, sertindole, molindone, pharmaceutically acceptable salts thereof, or combinations thereof.

In some embodiments, the anti-psychotic agent is a butyrophenone. The butyrophenone may comprise benperidol, bromperidol, droperidol, haloperidol, melperone, pipamperone, timiperone, spiperone, pharmaceutically acceptable salts thereof, or combinations thereof.

In some embodiments, the anti-psychotic agent is a diphenylbutylpiperidine. The diphenylbutylpiperidine may comprise fluspirilene, penfluridol, pimozide, pharmaceutically acceptable salts thereof, or combinations thereof.

In some embodiments, the anti-psychotic agent is a phenothiazine. The phenothiazine may comprise acepromazine, chlorpromazine, cyamemazine, dixyrazine, fluphenazine, levomepromazine, mesoridazine, perazine, periciazine, perphenazine, pipotiazine, prochlorperazine, promazine, promethazine, prothipendyl, thioproperazine, thioridazine, trifluoperazine, triflupromazine, pharmaceutically acceptable salts thereof, or combinations thereof.

In some embodiments, the anti-psychotic agent is a thioxanthene. The thioxanthene may comprise chlorprothixene, clopenthixol, flupentixol, thiothixene, zuclopenthixol, pharmaceutically acceptable salts thereof, or combinations thereof.

In some embodiments, the anti-psychotic agent is a benzamide. The benzamide may comprise sulpiride, sultopride, veralipride, amisulpride, nemonapride, remoxipride, levosulpiride, tiapride, pharmaceutically acceptable salts thereof, or combinations thereof.

In some embodiments, the anti-psychotic agent may comprise a tricyclic compound. The tricyclic compound may comprise carpipramine, clocapramine, clorotepine, clotiapine, loxapine, mosapramine, asenapine, clozapine, olanzapine, quetiapine, zotepine, pharmaceutically acceptable salts thereof, or combinations thereof.

In some embodiments, the anti-psychotic agent is a benzisoxazole or benzisothiazole. The benzisoxazole or benzisothiazole may comprise iloperidone, lurasidone, paliperidone, paliperidone palmitate, perospirone, risperidone, ziprasidone, pharmaceutically acceptable salts thereof, or combinations thereof.

In some embodiments, the anti-psychotic agent is a phenylpiperazine or a quinolinone. The phenylpiperazine or quinolinone may comprise aripiprazole, aripiprazole lauroxil, brexpiprazole, cariprazine, pharmaceutically acceptable salts thereof, or combinations thereof.

In one embodiment, the anti-psychotic agent is haloperidol or a pharmaceutically acceptable salt thereof. In another embodiment, the opioid antagonist is naloxone or a pharmaceutically acceptable salt thereof and the anti-psychotic agent is haloperidol or a pharmaceutically acceptable salt thereof. In another embodiment, the opioid antagonist is naltrexone or a pharmaceutically acceptable salt thereof and the anti-psychotic agent is haloperidol or a pharmaceutically acceptable salt thereof. In a further embodiment, the opioid antagonist is nalmefene or a pharmaceutically acceptable salt thereof and the anti-psychotic agent is haloperidol or a pharmaceutically acceptable salt thereof.

In certain embodiments, the anti-psychotic agent, per unit dose, comprises about 2 mg to about 40 mg, about 2 mg to about 20 mg, about 5 mg to about 15 mg, about 2 mg to about 10 mg, about 10 mg to about 20 mg, about 5 mg to about 10 mg, about 10 mg to about 15 mg, about 15 mg to about 20 mg, or about 7 mg to about 12 mg haloperidol or a pharmaceutically acceptable salt thereof suitable for intramuscular or subcutaneous administration.

In certain embodiments, the delivery systems and pharmaceutical compositions disclosed herein may further comprise an active agent comprising tranquilizers, CNS depressants, CNS stimulants, sedative hypnotics, or mixtures thereof.

In certain embodiments, the pharmaceutical composition and dosage forms disclosed herein may comprise from about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, or about 7% to about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 60%, about 70%, or about 80% (w/v) of an opioid antagonist, or a combination of an opioid antagonist, adjuvant, and/or antipsychotic agent, per dosage form. In certain embodiments, the pharmaceutical composition and dosage forms disclosed herein may comprise from about 0.1% to about 80%, from about 0.5% to about 30%, or from about 1% to about 10% (w/v) of an opioid antagonist, or a combination of an opioid antagonist, adjuvant, and/or antipsychotic agent, per dosage form.

Prophylactic Treatment

It is an object of certain embodiments of the present invention to provide a method to prevent or minimize an overdose of an opioid agonist in a subject that is at risk for exposure to an opioid agonist. For example, law enforcement personnel, first medical responders, or drug-sniffing canines can be pre-treated with an opioid antagonist according to the present invention prior to entering an environment or locale (e.g., a crime scene or emergency situation) where they suspect that opioids (e.g., fentanyl, carfentanyl or sufentanyl) may have been intentionally or unintentionally released, or are otherwise present. Also, workers at environmental disaster areas involving opioids may be pretreated to avoid toxicity of opioids that may be present in the environment. In the embodiments directed to methods of prophylactic treatment, the administered compositions can include, but not be limited to the pharmaceutical compositions as disclosed herein. For example, the administration of an opioid antagonist for prophylactic treatment can utilize the presently disclosed formulations for intramuscular or subcutaneous administration or can utilize oral, nasal, pulmonary, transdermal, rectal, intravenous, buccal or sublingual routes of administering opioid antagonists.

Pharmaceutically Acceptable Excipients

The pharmaceutical compositions according to the present invention may comprise one or more pharmaceutically acceptable carriers and excipients appropriate for intramuscular or subcutaneous administration. Examples of possible pharmaceutically acceptable carriers and excipients are described in the Handbook of Pharmaceutical Excipients, American Pharmaceutical Association (6$^{th}$ Edition, 2009 Publication), which is incorporated by reference herein. Carriers and excipients suitable for intramuscular and subcutaneous formulations include, but are not limited to, antioxidants, buffering agents, diluents, surfactants, solubilizers, stabilizers, hydrophilic polymers, additional absorption or permeability enhancers, preservatives, osmotic agents, isotonicity agents, pH adjusting agents, solvents, co-solvents, viscosity agents, gelling agents, suspending agents or combinations thereof.

Suitable surfactants for the formulations disclosed herein include, but are not limited to Polysorbate 80 NF, polyoxyethylene 20 sorbitan monolaurate, polyoxyethylene (4) sorbitan monolaurate, polyoxyethylene 20 sorbitan monopalmitate, polyoxyethylene 20 sorbitan monostearate, polyoxyethylene (4) sorbitan monostearate, polyoxyethylene 20 sorbitan tristearate, polyoxyethylene (5) sorbitan monooleate, polyoxyethylene 20 sorbitan trioleate, polyoxyethylene 20 sorbitan monoisostearate, sorbitan monooleate, sorbitan monolaurate, sorbitan monopalmitate, sorbitan monostearate, sorbitan trilaurate, sorbitan trioleate, sorbitan tristearate, and the like, and combinations thereof, Suitable isotonicity agents for the pharmaceutical compositions disclosed herein include, but are not limited to dextrose, lactose, sodium chloride, calcium chloride, magnesium chloride, sorbitol, sucrose, mannitol, trehalose, raffinose, various polyethylene glycol (PEG), hydroxyethyl starch, glycine, and the like, and combinations thereof.

Suitable suspending agents for the formulations disclosed herein include, but are not limited to microcrystalline cellulose, carboxymethylcellulose sodium NF, polyacrylic acid, magnesium aluminum silicate, xanthan gum, and the like, and mixtures thereof. In certain embodiments, the pharmaceutical compositions may include one or more suspending agents in an amount of from about 0.1 wt % to about 15 wt %, or from about 0.25 wt % to about 10 wt %, or from about 1 wt % to about 8 wt %, of the total weight of the pharmaceutical composition.

Method of Providing Overdose Rescue

In certain embodiments, the present disclosure is directed to a method of providing opioid overdose rescue to a subject in need thereof. The method comprises administering to a subject in need thereof an opioid antagonist, optionally an adjuvant, and optionally an antipsychotic agent, such that the onset of action of the antagonist is achieved in sufficient time to reverse or partially reverse the overdose. In certain embodiments, the present invention is intended to be urgently administered to a subject experiencing a medical emergency precipitated by opioid agonist overdose. In such circumstances, the pharmaceutical composition will typically be administered by a medical practitioner, emergency medical technician, law enforcement member, family member, acquaintance, or bystander post observing the subject experiencing the symptoms of opioid agonist overdose. In some embodiments, the method may further comprise, before the administering step, identifying that the subject is experiencing an opioid agonist overdose.

The opioid agonist overdose treated by the present invention can result from any overdose resulting from any opioid or combination of opioids currently known or those that would be readily appreciated by an ordinary skilled artisan (in formulation and medical fields) for such use, including but not limited to any of the following: alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl and derivatives, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol, pharmaceutically acceptable salts thereof, and combinations thereof.

In certain embodiments, the opioid antagonist is administered to a subject in an effective amount to counteract the opioid agonist overdose. In certain embodiments, the optional anti-psychotic agent is co-administered to a subject with an antagonist and an adjuvant in an effective amount to prevent, reduce, or counteract a manic behavior. The manic behavior may be a physically or mentally combative behavior seen in some subjects immediately post recovery from the overdose.

In some embodiments, the opioid antagonist, adjuvant, and the optional anti-psychotic agent are each administered separately. In other embodiments, the opioid antagonist, adjuvant, and the optional anti-psychotic agent are all administered together as a combination in a single dosage form. In one embodiment, the opioid antagonist and adjuvant may be administered together as a combination and the optional anti-psychotic agent may be administered separately. In one embodiment, the opioid antagonist and optional anti-psychotic agent may be administered together as a combination and the adjuvant may be administered separately. In one embodiment, the optional anti-psychotic agent and adjuvant may be administered together as a combination and the opioid antagonist may be administered separately.

In certain embodiments, the optional anti-psychotic agent is administered to a subject before the subject returns to consciousness. In this manner, the subject may already experience a therapeutic effect of the anti-psychotic agent post awakening or shortly thereafter, which may serve to prevent the subject from engaging in a physically or mentally combative behavior after rescue from the opioid agonist overdose.

In some embodiments, the opioid antagonist, adjuvant, and the optional anti-psychotic agent are all administered via the same route of administration, i.e., intramuscular or subcutaneous. In other embodiments, the opioid antagonist, adjuvant, and the optional anti-psychotic agent are administered via different routes of administration. For example, the optional anti-psychotic agent may be administered via intravenous administration, nasal administration, sublingual or buccal administration, or by inhalation.

In one embodiment, the opioid antagonist, adjuvant, and the optional anti-psychotic agent are both administered to a subject in need thereof via intramuscular administration.

In another embodiment, the opioid antagonist, adjuvant, and the optional anti-psychotic agent are administered to a subject in need thereof via subcutaneous administration.

In some embodiments, the opioid antagonist, adjuvant, and the optional anti-psychotic agent are administered concurrently, simultaneously, or sequentially.

The term "concurrently" as used herein means that a dose of one agent is administered prior to the end of the dosing interval of another agent. For example, a dose of an opioid antagonist with a particular dosing interval would be concurrently administered with an anti-psychotic agent dose when administered within the dosing interval of the opioid antagonist.

The term "simultaneously" as used herein means that a dose of one agent is administered approximately at the same time as another agent, regardless of whether the agents are administered separately via the same or different routes of administration or in a single pharmaceutical composition or dosage form. For example, a dose of an opioid antagonist may be administered separately from, but at the same time as, a dose of an anti-psychotic agent.

The term "sequentially" as used herein means that a dose of one agent is administered first and thereafter a dose of another agent is administered second. For example, a dose of an opioid antagonist may be administered first, and thereafter a dose of an anti-psychotic agent may be administered second. The subsequent administration of the second agent may be inside or outside the dosing interval of the first agent.

Other Indications

The pharmaceutical compositions, drug delivery devices and methods disclosed herein may alternatively be used for the treatment of alcohol dependence, constipation and other conditions that may be treated with opioid antagonists.

In certain embodiments, the present invention is directed to a method of treating alcohol dependence in a subject in need thereof. Thus, the method may comprise administering any of the pharmaceutical compositions disclosed herein to a subject in need thereof for the treatment of alcohol dependence and/or its symptoms. In some embodiments, the method may further comprise, before the administering step, identifying that the subject is experiencing a symptom of alcohol dependence.

In certain embodiments, the present invention is directed to a method of treating constipation in a subject in need thereof. Thus, the method may comprise administering any of the pharmaceutical compositions disclosed herein to a subject in need thereof for the treatment of constipation and/or its symptoms. In some embodiments, the method may further comprise, before the administering step, identifying that the subject is experiencing a symptom of constipation.

The amount of active agent in the pharmaceutical composition may be effective to treat, counteract, or reduce the severity of the target indication, e.g., opioid overdose, alcohol dependence, constipation, and/or one or more of their symptoms.

Drug Delivery Systems and Kits

In certain embodiments, the present invention is directed to a drug delivery system or to a kit containing an injection device and any of the pharmaceutical formulations (e.g., parenteral) disclosed herein. In certain embodiments, the injection device is pre-filled with the pharmaceutical formulation. In certain embodiments, the injection device comprises a syringe, a vial, an injection pen, or an autoinjector, which is pre-filled with the pharmaceutical formulation disclosed herein.

In certain embodiments, the drug delivery system or kit may comprise an active agent and an adjuvant in separate containers (e.g., separate vials, separate syringe barrels, separate compartments, and the like). In one embodiment, nalmefene or a pharmaceutically acceptable salt thereof may be in one container and an adjuvant (e.g., $MgCl_2$) may be in another container such that the nalmefene or pharmaceutically acceptable salt thereof may be mixed prior to administration.

In certain embodiments, the active agent (e.g., nalmefene or pharmaceutically acceptable salt thereof) in the drug delivery system or kit may be in solution or in powder form. In certain embodiments, the adjuvant in the drug delivery system or kit may be in solution or in powder form.

In one embodiment, the drug delivery system or kit may comprise an active agent (e.g., nalmefene or pharmaceutically acceptable salt thereof) solution in one container and an adjuvant (e.g., $MgCl_2$) solution in another container. The active agent solution and adjuvant solution may be mixed prior to administration. In one embodiment, the active agent solution may be in one compartment of an auto-injector and the adjuvant solution may be in another compartment in an auto-injector and the two solutions may be mixed in the auto-injector prior to administration. In another embodiment, the active agent solution may be in one vial, the adjuvant solution may be in another vial, and the contents of the vials may be mixed prior to administration (e.g, by transferring the content of one vial into another vial with a syringe and needle which could be part of the kit described herein).

In one embodiment, the drug delivery system or kit described herein may comprise an active agent (e.g., nalmefene or pharmaceutically acceptable salt thereof) solution in one container and an adjuvant (e.g., $MgCl_2$) powder in another container. The active agent solution and adjuvant powder may be mixed prior to administration. In one embodiment, the active agent solution may be in one compartment of an auto-injector and the adjuvant powder may be in another compartment in an auto-injector and the powder and solution may be mixed in the auto-injector prior to administration. In another embodiment, the active agent solution may be in one vial (or pre-filled syringe barrel or the like), the adjuvant powder may be in another vial, and the active agent solution may be added to the adjuvant powder (e.g., by transferring the active agent solution into the adjuvant powder container with a syringe and needle which could be part of the kit described herein) to suspend or dissolve the adjuvant powder prior to administration.

In one embodiment, the drug delivery system or kit described herein may comprise an active agent (e.g., nalmefene or pharmaceutically acceptable salt thereof) powder in one container and an adjuvant (e.g., $MgCl_2$) solution in another container. The active agent powder and adjuvant solution may be mixed prior to administration. In one embodiment, the active agent powder may be in one compartment of an auto-injector and the adjuvant solution may be in another compartment of an auto-injector and the powder and solution may be mixed in the auto-injector prior to administration. In another embodiment, the active agent powder may be in one vial, the adjuvant solution may be in another vial (or pre-filled syringe barrel or the like), and the adjuvant solution may be added to the active agent powder (e.g., by transferring the adjuvant solution into the active agent powder container with a syringe and needle which could be part of the kit described herein) to suspend or dissolve the active agent powder prior to administration.

In one embodiment, the drug delivery system or kit described herein may comprise an active agent (e.g., nalmefene or pharmaceutically acceptable salt thereof) powder in one container, an adjuvant (e.g., $MgCl_2$) powder in another container, and a solvent in yet another container. The active agent powder, adjuvant powder, and solvent may be mixed prior to administration. In one embodiment, the active agent powder may be in one compartment of an auto-injector, the adjuvant powder may be in another compartment of an auto-injector, and a solvent may be in yet another compartment of an auto injection such that the powders may be suspended or dissolved in the solvent prior to administration. In another embodiment, the active agent powder may be in one vial, the adjuvant powder may be in another vial, and the solvent may be in yet another vial (or pre-filled syringe barrel or the like), and the solvent may be added to the active agent powder and/or to the adjuvant powder (e.g., by transferring the solvent into the active agent powder and/or the adjuvant powder container(s) with a syringe and needle which could be part of the kit described herein) to suspend or dissolve the powders prior to administration.

In certain embodiments, the drug delivery system or kit described herein may comprise an active agent (e.g., nalmefene or pharmaceutically acceptable salt thereof) and an adjuvant (e.g., $MgCl_2$) combined together in a powder form in one container, and a pharmaceutically acceptable solvent is stored in another container, prior to administration. In one embodiment, the active agent powder and adjuvant powder may be mixed together in one compartment of an auto-injector and a pharmaceutically acceptable solvent may be stored in another compartment in an auto injection such that the powder mixture may be suspended or dissolved in the solvent prior to administration. In another embodiment, the active agent powder and the adjuvant powder may be mixed together in one vial, and the solvent may be in another vial (or pre-filled syringe barrel or the like), and the solvent may be added to the powder mixture (e.g., by transferring the solvent into the powder mixture container with a syringe and needle which could be part of the kit described herein) to suspend or dissolve the powder mixture prior to administration.

Concentration ranges and/or values of active agents and/or adjuvants expressed in % (w/v) disclosed previously refer to the final concentrations when all components are mixed together just prior to administration.

EXAMPLES

The following prophetic Examples 1-3 are set forth to assist in understanding the invention and should not be construed as specifically limiting the invention described and claimed herein. Such variations of the invention, including the substitution of any or all equivalents now known or later developed, which would be within the purview of those skilled in the art, and changes in formulation or minor changes in therapeutic design, are to be considered to fall within the scope of the invention incorporated herein.

Example 1

TABLE 1

| Component | Quantity per dose (mg) | Concentration (mg/ml) |
| --- | --- | --- |
| Nalmefene or a pharmaceutically acceptable salt thereof | 5 | 5 |
| Arginine | 50 | 50 |

Aqueous solutions are prepared and sodium chloride is added to adjust tonicity and hydrochloric acid is added to adjust pH to about 3.8 to 4.5.

The solution is contained in a device suitable for intramuscular or subcutaneous administration.

Example 2

TABLE 2

| Component | Quantity per dose (mg) | Concentration (mg/ml) |
| --- | --- | --- |
| Naloxone or a pharmaceutically acceptable salt thereof | 1 | 2 |
| Nicotinic acid | 10 | 20 |

Aqueous solutions are prepared and sodium chloride is added to adjust tonicity and hydrochloric acid is added to adjust pH to about 3.8 to 4.5.

The solution is contained in a device suitable for intramuscular or subcutaneous administration.

Example 3

TABLE 3

| Component | Quantity per dose (mg) | Concentration (mg/ml) |
|---|---|---|
| Naloxone or a pharmaceutically acceptable salt thereof | 5 | 5 |
| Magnesium Chloride | 10 | 10 |

Aqueous solutions are prepared and hydrochloric acid is added to adjust pH to about 3.8 to 4.5. The solution is contained in a device suitable for intramuscular or subcutaneous administration.

The following examples set forth a study performed in dogs to assist in understanding the invention and should not be construed as specifically limiting the invention described and claimed herein. Such variations of the invention, including the substitution of any or all equivalents now known or later developed, which would be within the purview of those skilled in the art, and changes in formulation or minor changes in therapeutic design, are to be considered to fall within the scope of the invention incorporated herein.

Example 4

Formulations of nalmefene hydrochloride alone, as well as of nalmefene hydrochloride and an adjuvant selected from L-Arginine, $MgCl_2$, or Nicotinic Acid, were prepared in the dosages summarized in Table 4 below (calculated based on nalmefene free base). The formulations were administered intramuscularly to three canine subjects. Blood samples were drawn pre-dose and at 1 minute, 3 minutes, 6 minutes, 10 minutes, 20 minutes, 1 hour, and 3 hours post-dose.

TABLE 4

Study Design

| Group Number | Test Article Formulation | Dosing Route | N= | Dose (mg) | Dosing Concentration (mg/mL) | Dose Volume (mL) | Vehicle |
|---|---|---|---|---|---|---|---|
| 1 | Nalmefene | IM | 3 | 0.1 | 0.5 | 0.2 | Saline (0.9% (w/v) NaCl) |
| 2 | Nalmefene | IM | 3 | 0.25 | 1.25 | 0.2 | Saline (0.9% (w/v) NaCl) |
| 3 | Nalmefene | IM | 3 | 1.0 | 5.0 | 0.2 | Saline (0.9% (w/v) NaCl) |
| 4 | Nalmefene + 20% (w/v) Arginine | IM | 3 | 0.25 | 1.25 | 0.2 | L-Arginine |
| 5 | Nalmefene + 5% (w/v) $MgCl_2$ | IM | 3 | 0.25 | 1.25 | 0.2 | $MgCl_2$ |
| 6 | Nalmefene + 1% (w/v) Nicotinic Acid | IM | 3 | 0.25 | 1.25 | 0.2 | Nicotinic Acid |
| 7 | Nalmefene + 5% (w/v) $MgCl_2$ | IM | 3 | 0.25 | 1.25 | 0.2 | $MgCl_2$ |
| 8 | Nalmefene + 10% (w/v) $MgCl_2$ | IM | 3 | 0.25 | 1.25 | 0.2 | $MgCl_2$ |
| 9 | Nalmefene + 20% (w/v) $MgCl_2$ | IM | 3 | 0.25 | 1.25 | 0.2 | $MgCl_2$ |

The comparative mean plasma concentration profiles of nalmefene at different doses (group 1: 0.1 mg, group 2: 0.25 mg, and group 3: 1 mg) after intramuscular administration in three canine subjects are depicted in FIG. 1.

Figure 2:
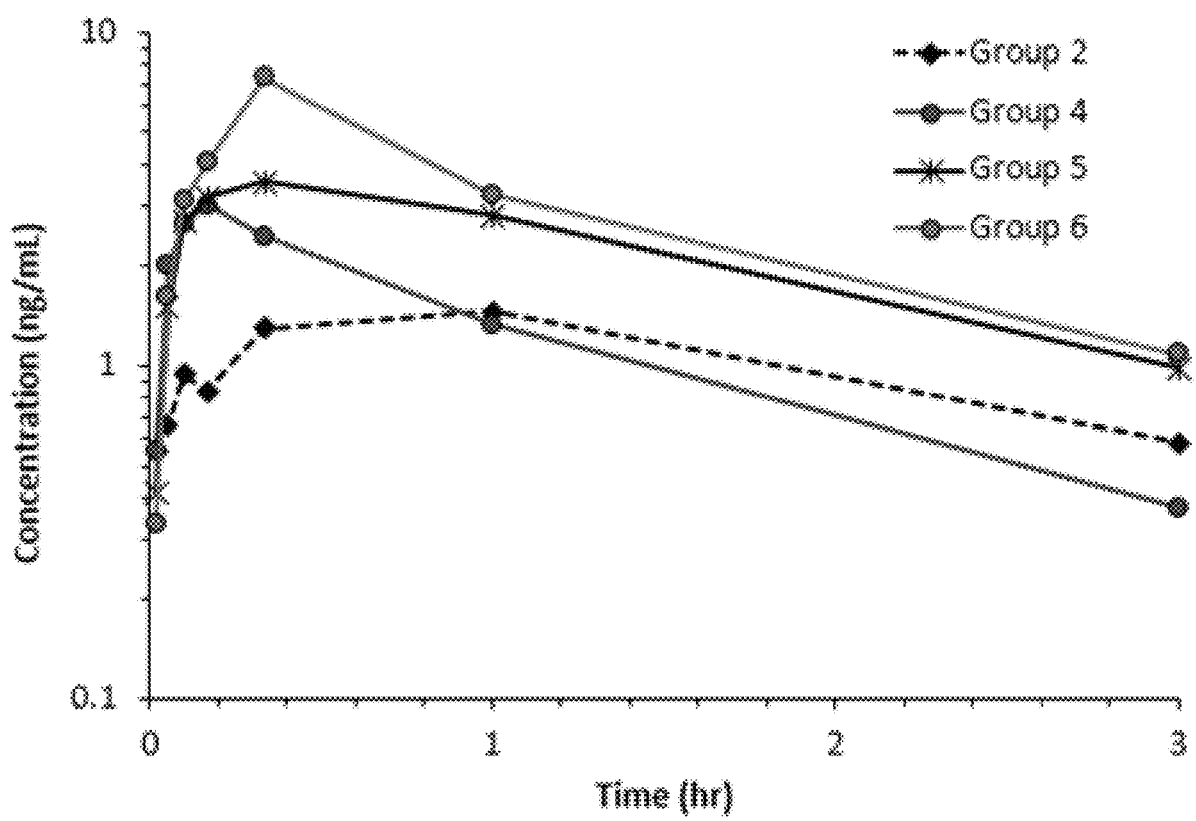
FIG. 2 depicts the mean plasma concentration profiles of nalmefene in three canine subjects post intramuscular administration of various nalmefene formulations (dose of 0.25 mg each) with selected adjuvants.
Figure 3:
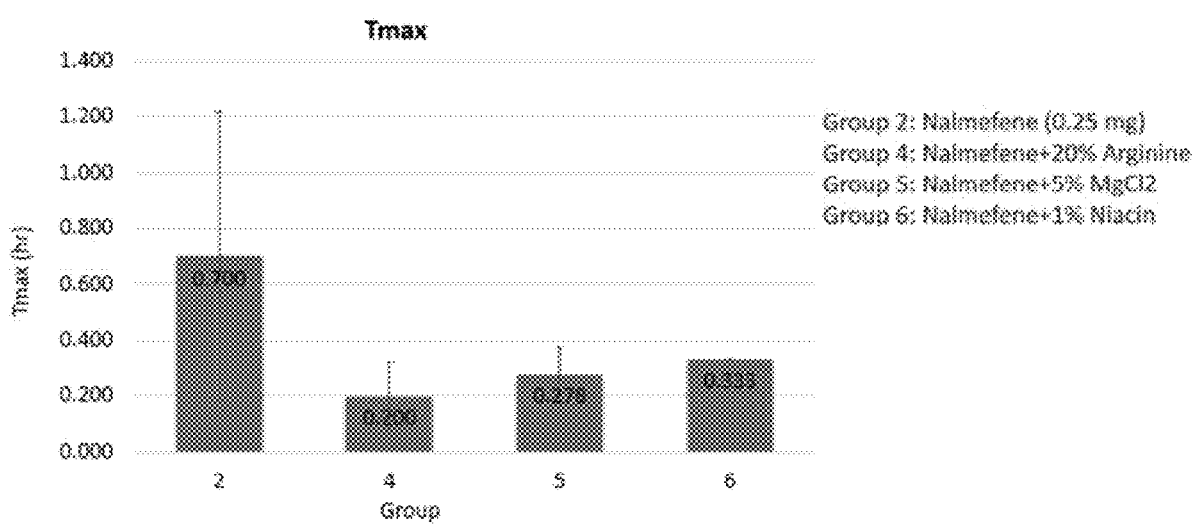
FIG. 3 depicts the $T_{max}$ values of nalmefene in three canine subjects after intramuscular administration of various nalmefene formulations (dose of 0.25 mg each) formulated with and without selected adjuvants.

The comparative mean plasma concentration profiles of nalmefene (dose of 0.25 mg) in the presence of various adjuvants (groups 4-6) in three canine subjects after intramuscular administration are depicted in FIG. 2. The comparative $T_{max}$ values of nalmefene (dose of 0.25 mg) in the presence of various adjuvants (groups 4-6) in three canine subjects after intramuscular administration are depicted in FIG. 3. The resulting mean pharmacokinetic data of the study performed on groups 4-6 are summarized in Table 5 below.

Figure 4:
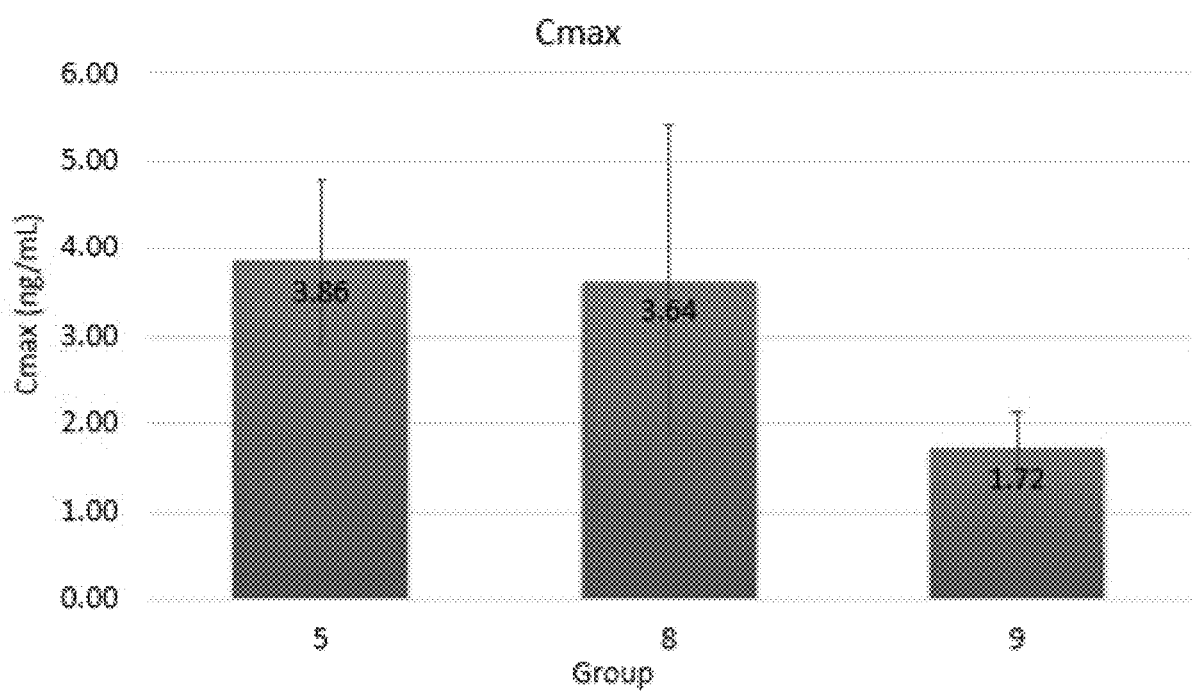
FIG. 4 depicts the $C_{max}$ of nalmefene in three canine subjects after intramuscular administration of three formulations in which nalmefene (dose of 0.25 mg each) was formulated with 5% (w/v), 10% (w/v), and 20% (w/v) $MgCl_2$, respectively.

The comparative $C_{max}$ of nalmefene obtained from canine subjects that were administered nalmefene in the presence of 5% (w/v), 10% (w/v), and 20% (w/v) $MgCl_2$ per pharmaceutical composition (groups 5, 8-9) are depicted in FIG. 4.

TABLE 5

Comparative Mean PK Parameters of Nalmefene (0.25 mg, 1.25 mg/mL) in the Presence of Various Adjuvants after IM Administration in Dogs

| | Enhancers | | | |
| --- | --- | --- | --- | --- |
| | No Enhancer/ Adjuvant | 20% (w/v) Arginine | 5% (w/v) $MgCl_2$ | 1% (w/v) Nicotinic Acid |
| | Concentration of Nalmefene (ng/mL) | | | |
| Time (hours (min)) | | | | |
| 0 hours (pre-dose) | BLOQ* | BLOQ* | BLOQ* | BLOQ* |
| 0.0167 hours (1 minute) | 0.556 | 0.554 | 0.419 | 0.337 |
| 0.0500 hours (3 minutes) | 0.664 | 2.01 | 1.49 | 1.60 |
| 0.100 hours (6 minutes) | 0.940 | 2.63 | 2.68 | 3.11 |
| 0.167 hours (10 minutes) | 0.838 | 3.02 | 3.17 | 4.05 |
| 0.333 hours (20 minutes) | 1.30 | 2.43 | 3.55 | 7.32 |
| 1.00 hours | 1.45 | 1.33 | 2.81 | 3.23 |
| 3.00 hours | 0.587 | 0.377 | 0.980 | 1.09 |
| Parameter | | | | |
| Animal Weight (kg) | 13.1 | 10.8 | 12.4 | 12.2 |
| Dose (mg/kg) | 0.0194 | 0.0232 | 0.0203 | 0.0206 |
| $C_{max}$ (ng/mL) | 1.49 | 3.19 | 3.86 | 7.32 |
| $T_{max}$ (hr) | 0.700 | 0.200 | 0.278 | 0.333 |
| $T_{1/2}$ (hr) | 1.45 | 0.912 | 1.39 | ND** |
| $MRT_{last}$ (hr) | 1.20 | 0.868 | 1.07 | 0.958 |
| $AUC_{last}$ (ng · hr/mL) | 3.25 | 3.76 | 6.81 | 9.17 |
| $AUC_\infty$ (ng · hr/mL) | 4.31 | 3.80 | 9.27 | ND** |
| Dose-normalized Values | | | | |
| $AUC_{last}/D$ (ng · hr · kg/mL/mg) | 169 | 161 | 336 | 453 |
| $AUC_\infty$ (ng · hr · kg/mL/mg) | 192 | 164 | 446 | ND** |

*BLOQ means Below Level Of Quantification
**ND means Not Detected

Example 5

The primary objectives of the clinical study were to assess the pharmacokinetics of nalmefene following parenteral administration of various doses and/or formulations of nalmefene hydrochloride and to assess the early systemic exposure to nalmefene following intramuscular administration. The secondary objective of the clinical study was to evaluate the safety and tolerability of nalmefene hydrochloride following parenteral administration.

The study designed was an open-label, randomized, single dose, crossover study in healthy male and female subjects to compare the pharmacokinetic profiles of nalmefene following administration of various routes, doses and/or formulations of nalmefene hydrochloride.

Formulations of nalmefene alone, as well as of nalmefene in combination with various concentrations of $MgCl_2$, were prepared as summarized in Table 6 below. The formulations were administered intramuscularly into the deltoid muscle using 1 mL injections to eight human subjects to evaluate the effect of $MgCl_2$ on the rate and extent of absorption of a 1.5 mg dose of nalmefene. A ninth subject was administered only a formulation of 1.5 mg nalmefene in 1.0 mL of 0.9% $MgCl_2$. All nalmefene doses in this example were calculated based on nalmefene free base.

TABLE 6

Study Design

| Group | No. of Subjects Treated | Treatment |
| --- | --- | --- |
| 1 | 8 subjects | Nalmefene 1.5 mg in 1.0 mL of 0% $MgCl_2$ |
| 2 | 9 subjects | Nalmefene 1.5 mg in 1.0 mL of 0.9% $MgCl_2$ |
| 3 | 8 subjects | Nalmefene 1.5 mg in 1.0 mL of 2.8% $MgCl_2$ |
| 4 | 8 subjects | Nalmefene 1.5 mg in 1.0 mL of 4.7% $MgCl_2$ |

Table 7 below summarizes the pharmacokinetic data obtained from subjects treated with the nalmefene formulations summarized in Table 6. All PK data is expressed as nalmefene free base.

TABLE 7

Comparative PK Parameters of Nalmefene (1.5 mg/mL) in the Presence of Various Concentrations of $MgCl_2$ after IM Administration in Human Subjects

|  | 0% (w/v) $MgCl_2$ | 0.9% (w/v) $MgCl_2$ | 2.8% (w/v) $MgCl_2$ | 4.7% (w/v) $MgCl_2$ |
|---|---|---|---|---|
| Mean $C_{max}$ (ng/mL) | 9.211 | 16.022 | 10.538 | 7.35 |
| Individual min $C_{max}$ (ng/mL) | 5.31 | 11.7 | 7.04 | 4.76 |
| Individual max $C_{max}$ (ng/mL) | 12.1 | 20 | 17.9 | 9.71 |
| Mean $T_{max}$ (hours(min)) | 0.16 (9.643) | 0.14 (8.889) | 0.23 (14.063) | 0.49 (29.375) |
| Individual min $T_{max}$ (hours (min)) | 0.13 (7.5) | 0.08 (5) | 0.17 (10) | 0.33 (20) |
| Individual max $T_{max}$ (hours (min)) | 0.21 (12.5) | 0.21 (12.5) | 0.33 (20) | 1 (60) |
| Mean $AUC_{0-2.5}$ (ng · hr/mL (ng · min/mL)) | 0.05 (2.75) | 0.10 (6.133) | 0.02 (1.256) | 0.01 (0.793) |
| Individual min $AUC_{0-2.5}$ (ng · hr/mL (ng · min/mL)) | 0.004 (0.23) | 0.007 (0.4) | 0.003 (0.2) | 0.007 (0.43) |
| Individual max $AUC_{0-2.5}$ (ng · hr/mL (ng · min/mL)) | 0.13 (8.06) | 0.31 (18.51) | 0.06 (3.8) | 0.03 (1.62) |
| Mean $AUC_{0-5}$ (ng · hr/mL (ng · min/mL)) | 0.20 (12.193) | 0.45 (27.241) | 0.12 (7.247) | 0.07 (3.901) |
| Individual min $AUC_{0-5}$ (ng · hr/mL (ng · min/mL)) | 0.08 (4.91) | 0.13 (7.7) | 0.05 (2.71) | 0.04 (2.15) |
| Individual max $AUC_{0-5}$ (ng · hr/mL (ng · min/mL)) | 0.44 (26.2) | 0.94 (56.64) | 0.38 (22.6) | 0.11 (6.45) |
| Mean $AUC_{0-7.5}$ (ng · hr/mL (ng · min/mL)) | 0.48 (28.688) | 1.01 (60.403) | 0.35 (21.014) | 0.18 (10.723) |
| Individual min $AUC_{0-7.5}$ (ng · hr/mL (ng · min/mL)) | 0.22 (12.99) | 0.38 (22.81) | 0.15 (8.88) | 0.11 (6.34) |
| Individual max $AUC_{0-7.5}$ (ng · hr/mL (ng · min/mL)) | 0.82 (49.28) | 1.72 (103.261) | 0.95 (57.23) | 0.26 (15.8) |
| Mean $AUC_{0-10}$ (ng · hr/mL (ng · min/mL)) | 0.83 (49.877) | 1.61 (96.805) | 0.69 (41.303) | 0.35 (21.19) |
| Individual min $AUC_{0-10}$ (ng · hr/mL (ng · min/mL)) | 0.40 (24.14) | 0.75 (44.7) | 0.36 (21.53) | 0.22 (13.36) |
| Individual max $AUC_{0-10}$ (ng · hr/mL (ng · min/mL)) | 1.25 (75.15) | 2.49 (149.39) | 1.63 (97.85) | 0.56 (33.8) |
| Mean $AUC_{0-12.5}$ (ng · hr/mL (ng · min/mL)) | 1.20 (71.988) | 2.20 (131.758) | 1.08 (64.692) | 0.56 (33.837) |
| Individual min $AUC_{0-12.5}$ (ng · hr/mL (ng · min/mL)) | 0.62 (37.08) | 1.20 (72.2) | 0.62 (37.2) | 0.38 (22.61) |
| Individual max $AUC_{0-12.5}$ (ng · hr/mL (ng · min/mL)) | 1.65 (99.29) | 3.18 (190.64) | 2.35 (141.23) | 0.91 (54.66) |
| Mean $AUC_{0-15}$ (ng · hr/mL (ng · min/mL)) | 1.54 (92.12) | 2.72 (163.334) | 1.48 (88.877) | 0.80 (47.998) |
| Individual min $AUC_{0-15}$ (ng · hr/mL (ng · min/mL)) | 0.83 (49.95) | 1.62 (96.91) | 0.88 (53) | 0.50 (30.17) |
| Individual max $AUC_{0-15}$ (ng · hr/mL (ng · min/mL)) | 2.01 (120.61) | 3.80 (227.89) | 3.08 (184.63) | 1.29 (77.28) |
| Mean $AUC_{0-20}$ (ng · hr/mL (ng · min/mL)) | 2.11 (126.448) | 3.62 (216.968) | 2.26 (135.311) | 1.32 (79.204) |
| Individual min $AUC_{0-20}$ (ng · hr/mL (ng · min/mL)) | 1.23 (73.7) | 2.34 (140.51) | 1.32 (78.91) | 0.65 (38.84) |
| Individual max $AUC_{0-20}$ (ng · hr/mL (ng · min/mL)) | 2.58 (154.91) | 4.84 (290.394) | 4.34 (260.1) | 2.08 (124.92) |

TABLE 7-continued

Comparative PK Parameters of Nalmefene (1.5 mg/mL) in the Presence of Various Concentrations of $MgCl_2$ after IM Administration in Human Subjects

| | 0% (w/v) $MgCl_2$ | 0.9% (w/v) $MgCl_2$ | 2.8% (w/v) $MgCl_2$ | 4.7% (w/v) $MgCl_2$ |
|---|---|---|---|---|
| Mean $AUC_{0-last}$ (ng · hr/mL (ng · min/mL)) | 23.53 (1412.08) | 26.46 (1587.318) | 26.90 (1613.989) | 24.99 (1499.201) |
| Individual min $AUC_{0-last}$ (ng · hr/mL (ng · min/mL)) | 20.13 (1207.91) | 20.63 (1237.63) | 20.52 (1231) | 21.54 (1292.35) |
| Individual max $AUC_{0-last}$ (ng · hr/mL (ng · min/mL)) | 27.91 (1674.83) | 32.97 (1978.09) | 45.73 (2744) | 27.84 (1670.39) |

The mean concentration of nalmefene in subjects treated with 1.5 mg/mL nalmefene in the presence of 0% (w/v), 0.9% (w/v), 2.8% (w/v), and 4.7% (w/v) $MgCl_2$ per parenteral formulation is depicted in FIG. 5, respectively.

In the foregoing description, numerous specific details are set forth, such as specific materials, dimensions, processes parameters, etc., to provide a thorough understanding of the present invention. The particular features, structures, materials, or characteristics may be combined in any suitable manner in one or more embodiments. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is simply intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. Reference throughout this specification to "an embodiment", "certain embodiments", or "one embodiment" means that a particular feature, structure, or characteristic described in connection with the embodiment is included in at least one embodiment. Thus, the appearances of the phrase "an embodiment", "certain embodiments", or "one embodiment" in various places throughout this specification are not necessarily all referring to the same embodiment.

The present invention has been described with reference to specific exemplary embodiments thereof. The specification and drawings are, accordingly, to be regarded in an illustrative rather than a restrictive sense. Various modifications of the invention in addition to those shown and described herein will become apparent to those skilled in the art and are intended to fall within the scope of the appended claims.

What is claimed is:

1. A parenteral formulation comprising an aqueous solution comprising about 1.5 mg of nalmefene free base or an equivalent amount of a pharmaceutically acceptable salt thereof and about 0.5% to about 1.0% (w/v) of a parenterally acceptable adjuvant, wherein the formulation provides a mean time to maximum plasma concentration of nalmefene ($T_{max}$) shorter than the mean time to maximum plasma concentration of nalmefene of a comparative formulation without the said adjuvant, post intramuscular or subcutaneous injection to a population of subjects, wherein the adjuvant is magnesium chloride.

2. The parenteral formulation of claim 1, wherein the mean $T_{max}$ of the formulation is about 1.1 times shorter, about 1.2 times shorter, or about 1.3 times shorter than that of the comparative formulation without the adjuvant.

3. The parenteral formulation of claim 1, wherein the formulation comprises about 0.9% (w/v) of magnesium chloride.

4. The parenteral formulation of claim 1, comprising nalmefene hydrochloride in an amount equivalent to 1.5 mg nalmefene free base.

5. The parenteral formulation of claim 1, wherein the formulation provides a mean time to maximum plasma concentration of nalmefene ($T_{max}$) shorter than the mean time to maximum plasma concentration of nalmefene of a comparative formulation without the said adjuvant, post intramuscular injection to a population of subjects.

6. The parenteral formulation of claim 1, wherein the formulation provides a mean time to maximum plasma concentration of nalmefene ($T_{max}$) shorter than the mean time to maximum plasma concentration of nalmefene of a comparative formulation without the said adjuvant, post subcutaneous injection to a population of subjects.

7. A parenteral formulation comprising an aqueous solution comprising about 1.5 mg of nalmefene hydrochloride in an amount equivalent to 1.5 mg nalmefene free base and about 0.9% (w/v) of a parenterally acceptable adjuvant, wherein the formulation provides a mean time to maximum plasma concentration of nalmefene ($T_{max}$) shorter than the mean time to maximum plasma concentration of nalmefene of a comparative formulation without the said adjuvant, post intramuscular injection to a population of subjects, wherein the adjuvant is magnesium chloride.

* * * * *